United States Patent [19]
Garcia et al.

[11] Patent Number: 6,065,488
[45] Date of Patent: May 23, 2000

[54] FLUID SAMPLING TOOL

[75] Inventors: Anthony R. Garcia, Espanola; Roger G. Johnston, Los Alamos; Ronald K. Martinez, Santa Cruz, all of N.Mex.

[73] Assignee: The Regents of the University of California, Los Alamos, N.Mex.

[21] Appl. No.: 09/209,588

[22] Filed: Dec. 11, 1998

[51] Int. Cl.[7] .................................................. F16K 43/00
[52] U.S. Cl. ............................... 137/318; 137/317; 73/52
[58] Field of Search ..................................... 137/318, 319, 137/317; 73/52, 152.01, 152.18, 152.23, 152.26, 863.81

[56] References Cited

U.S. PATENT DOCUMENTS

| | | | |
|---|---|---|---|
| 3,868,854 | 3/1975 | Travor et al. ............................ | 137/318 |
| 5,052,427 | 10/1991 | Butler et al. ............................ | 137/318 |
| 5,558,140 | 9/1996 | Clark ........................................ | 141/98 |
| 5,704,383 | 1/1998 | Kammeraad et al. .................... | 137/15 |
| 5,775,390 | 7/1998 | Mohn ...................................... | 137/318 |

*Primary Examiner*—David J. Walczak
*Attorney, Agent, or Firm*—Samuel L. Borkowsky

[57] ABSTRACT

A fluid-sampling tool for obtaining a fluid sample from a container. When used in combination with a rotatable drill, the tool bores a hole into a container wall, withdraws a fluid sample from the container, and seals the borehole. The tool collects fluid sample without exposing the operator or the environment to the fluid or to wall shavings from the container.

11 Claims, 5 Drawing Sheets

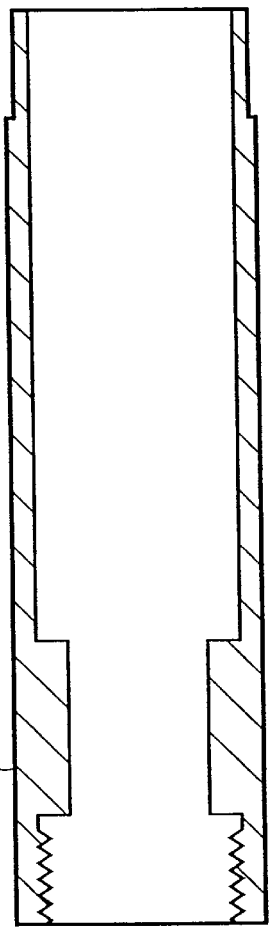
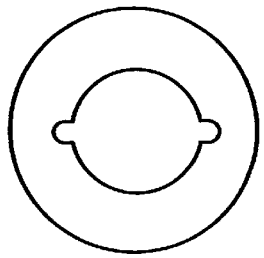
*Fig. 3b*
*Fig. 3a*
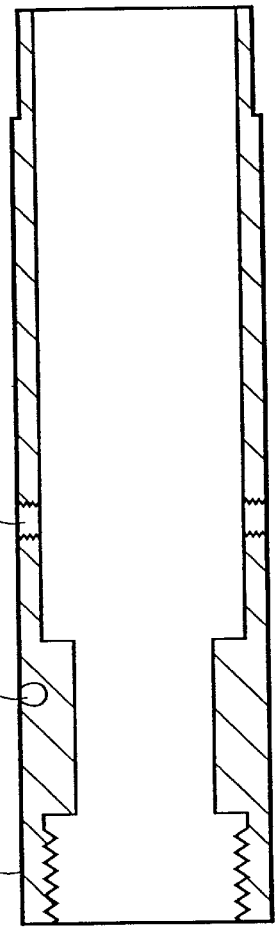
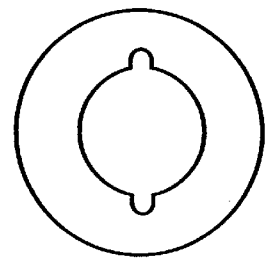
*Fig. 3d*
*Fig. 3c*

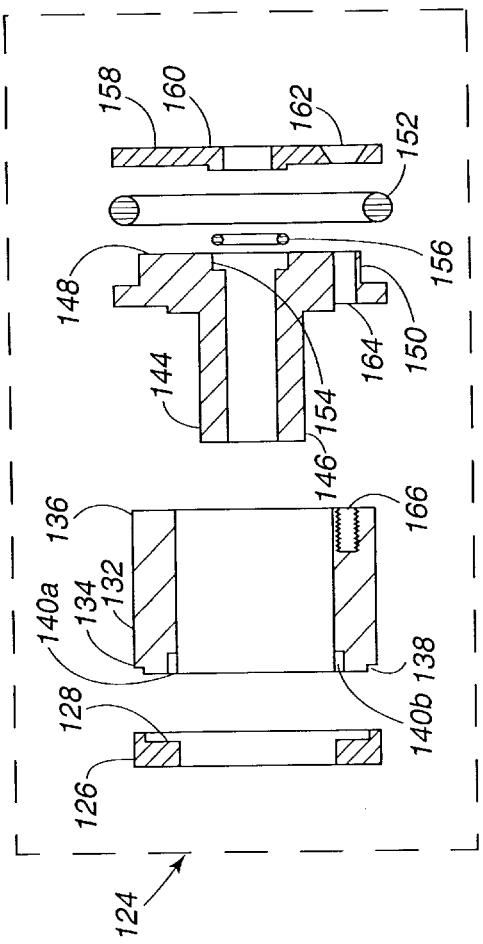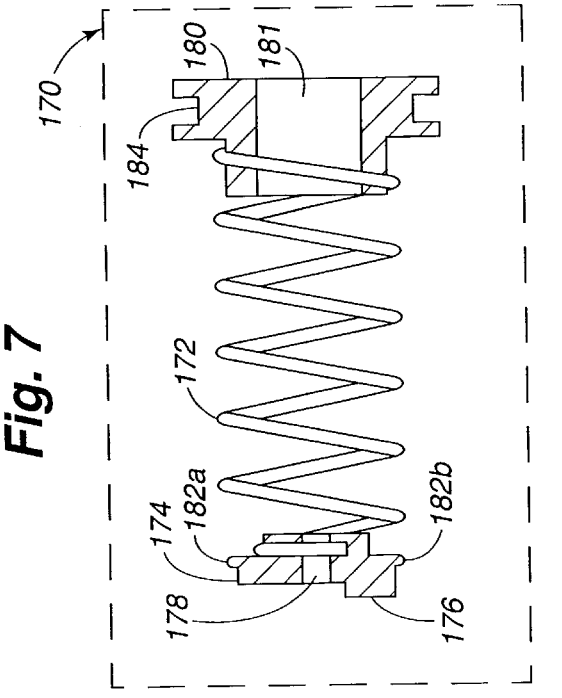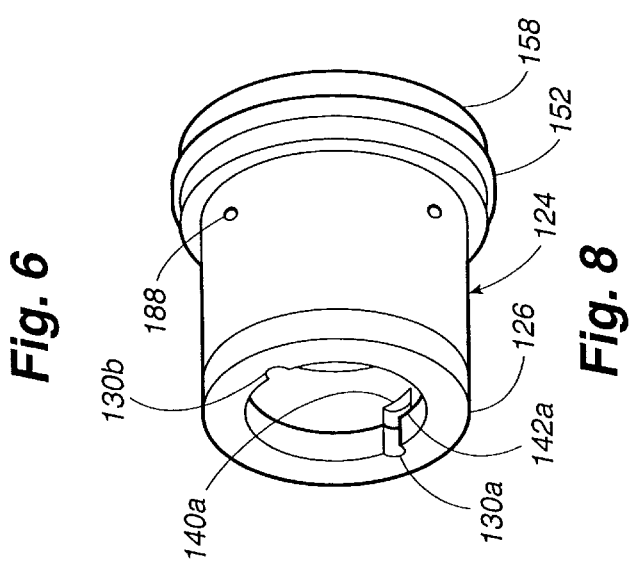

FLUID SAMPLING TOOL

FIELD OF THE INVENTION

The present invention relates generally to chemical sampling tools and, more particularly, to tools that allow the withdrawal of a fluid sample from a sealed container without spillage. This invention was made with government support under Contract No. W-7405-ENG-36 awarded by the U.S. Department of Energy to The Regents to the University of California. The U.S. Government has certain rights in the invention.

BACKGROUND OF THE INVENTION

The treatment and disposal of stored hazardous waste is a challenge. It is often necessary to store waste in a container since, at present, there may be no effective procedure for treating it. It also may be that the waste is not sufficiently characterized to make a determination of the appropriate treatment procedure. Thus, large quantities of untreated waste remain stored in containers and are awaiting treatment.

A typical waste storage container for a liquid waste is a metal drum. Waste is poured into the container, and a lid is sealed to the container to prevent the waste from escaping. Since an analysis of the waste composition from a sealed container may be necessary before an appropriate treatment and disposal procedure is implemented, a device for extracting a sample of waste from a sealed container is required.

Similar devices would be useful for extracting samples from munitions, which may contain dangerous chemicals. Importantly, during a sampling procedure, the user must avoid exposure to the material being sampled while obtaining a sample, and while transporting the sample to a site for analysis.

Devices that allow one to sample the fluid contents of sealed containers are known. In U.S. Pat. No. 5,704,383 by D. A. Kammeraad et al. entitled "Tool and Method for Removing Fluid From Container" which issued Jan. 6, 1998, a tool for tapping and removing fluid from a container is described. A frustoconically-shaped shank having a threaded outer surface sealingly engages the container wall as the shank is advanced into the container. Opposing inlets in the bit communicate with an internal passageway within the shank to allow fluid from the container to enter the tool. The tool is provided with a sealing surface that deforms the container wall while providing a seal between the sealing surface and the wall. Advancement of the frustoconically-shaped shank into the container wall increases the borehole size. An assembly attached to the shank houses a piston, which serves as a valve for preventing fluid in the shank passageway from escaping to the outside. A fluid collection unit can be attached to the valve assembly to obtain fluid samples.

In U.S. Pat. No. 5,558,140 by J. E. Clark II entitled "Device For Draining Fluid From a Container" which issued Sep. 24, 1996, a fluid draining device for removing oil is described. The device has a threaded screw with a sharpened puncturing tip and an internal fluid channel with at least one opening just behind the tip. It also has a threaded screw guide connected to a strap, which can be wrapped around a container and tightened. An opening in the strap coaxial with the bore of the screw guide allows the screw to pass through the strap. An optional sealing material placed in between the strap and the container wall may be used to provide a seal with the wall.

The '383 and '140 patents describe tools that must first be attached to the container. In a separate procedure, a sample of fluid from the container may be obtained with the attached tool. A portable tool for rapidly sampling fluid from a sealed container in a single step while preventing exposure to the contents is clearly desirable.

Therefore, an object of the invention is to provide a portable fluid-sampling tool for collecting fluid from a sealed container in a single step without exposing the user or the environment to the fluid.

Another object of the invention is to provide a fluid sampling tool that can be drilled into a sealed container without exposing the user to wall shavings created during drilling.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the objects and purposes of the present invention as embodied and broadly described herein, the present invention includes a tool for collecting a fluid sample through a container wall. The tool has an elongated drilling member having a drilling end, a piercing end, an inlet near the drilling end, an outlet at the piercing end, and an internal passageway providing fluid communication between the inlet and the outlet. The drilling member also has an externally threaded portion between the drilling end and the piercing end. The tool also has a means for rotating the drilling member whereby the drilling end of the drilling member drills a borehole into the container wall, whereby wall shavings, i.e. kerf, are generated. When the inlet near the drilling end enters the borehole, fluid enters the drilling member through the inlet and flows into the internal passageway inside the drilling member. The tool also includes a means for retracting the drilling member from the borehole. The tool also includes a chemical sealant and a means for forcing the chemical sealant into the borehole to seal the borehole. The tool also includes a means for withdrawing fluid through the piercing end of said drilling member. The fluid withdrawing means can be an evacuated container having an open end sealed with a septum.

Preferably, an external marking such as a phosphorescent stripe-type marking, is included with the present invention to determine its progress while obtaining a fluid sample. The location of the marking may be chosen such that when a sample of fluid has been obtained, and sealant has been delivered into the borehole, the marking is no longer visible.

The present invention provides a tool for drilling a borehole in a container, sampling fluid from the container through the borehole, and sealing the borehole, all in one continuous operation. Thus, the present invention offers clear advantages when compared to tools that must first be attached to a container in one operation and then, in a separate operation, be used as a conduit for the removal of a sample of fluid therein.

BRIEF DESCRIPTION OF THE DRAWINGS

The accompanying drawings, which are incorporated in and form a part of the specification, illustrate embodiments of the present invention and, together with the description, serve to explain the principles of the invention. In the Figures:

FIGS. 3a–d show cross-sectional side and top views of the barrel housing of the invention;

FIG. 6 shows a cross-sectional side view of the spring assembly compressed into the piston of the invention;

FIG. 7 shows an exploded cross-sectional side view of the piston of the invention;

FIG. 8 shows a perspective side view of the piston of the invention; and

FIG. 9 shows a perspective side view of the spring assembly of the invention.

DETAILED DESCRIPTION OF THE INVENTION

The present invention provides a fluid-sampling tool for obtaining a fluid sample from a sealed container. The fluid sample may be a gas, a liquid, or a free-flowing powder. When used in combination with a rotatable drill, the tool bores a hole into a container wall, extracts and collects a fluid sample from the container, and seals the borehole.

Reference will now be made to the present preferred embodiments of the invention, examples of which are illustrated in the accompanying drawings. Similar or identical structure is identified using identical callouts.

Figure 1:
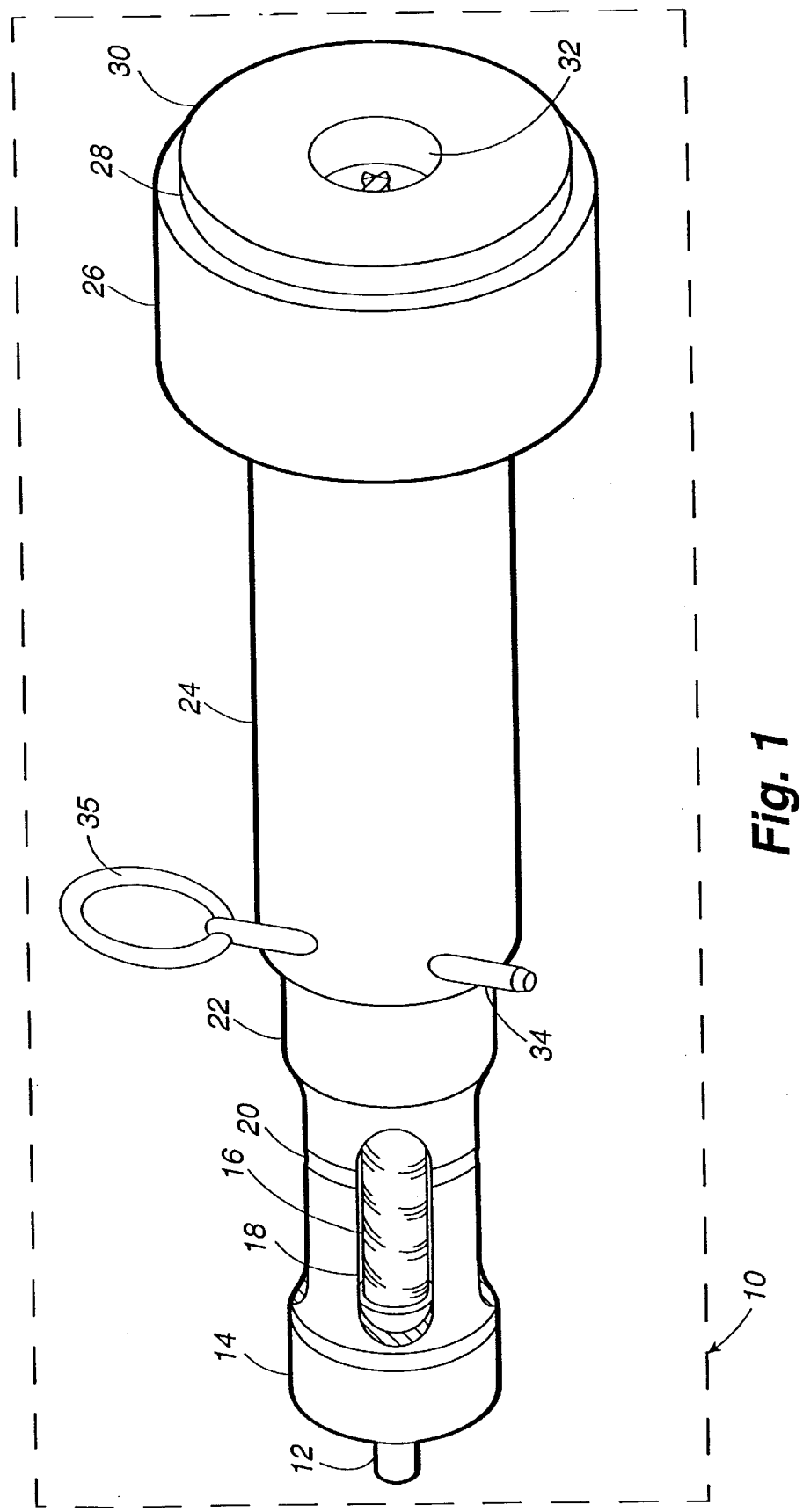
FIG. 1 shows a perspective side-view of the invention.

Turning now to the figures, FIG. 1 shows a perspective side view of the present invention. Fluid sampling tool 10 has a cylindrical shape and includes a shaft 12 for engagement with a rotatable drill chuck (not shown). Shaft 12 is connected to sample container housing 14, which houses a tubular sample container 16. Sample container housing 14 can be made from a transparent material such as polycarbonate, or from a non-transparent material such as aluminum; if a non-transparent material is chosen, then sample container housing 14 includes at least one port 18 to view container 16 during operation to verify that fluid is being collected therein. Phosphorescent stripe 20 encircles housing 14 at a chosen location. A tubular barrel housing 22 is threadably attached to sample container housing 14. Barrel housing 22 is surrounded by a sleeve 24, through which it slides during operation. A head member 26 is attached to sleeve 24, and a flexible sealing member 28 is attached to head member 26 to provide a sealing surface 30 for sealing tool 10 against a container wall during operation. An opening 32 in sealing member 28 provides an exit for a drilling member inside barrel housing 22 and for sealant inside head member 26. A pin 34 with an attached pull-ring 35, can be engaged to housing 14 and sleeve 24 to prevent barrel housing 22 from sliding within sleeve 24 when tool 10 is not in use.

Figure 2:
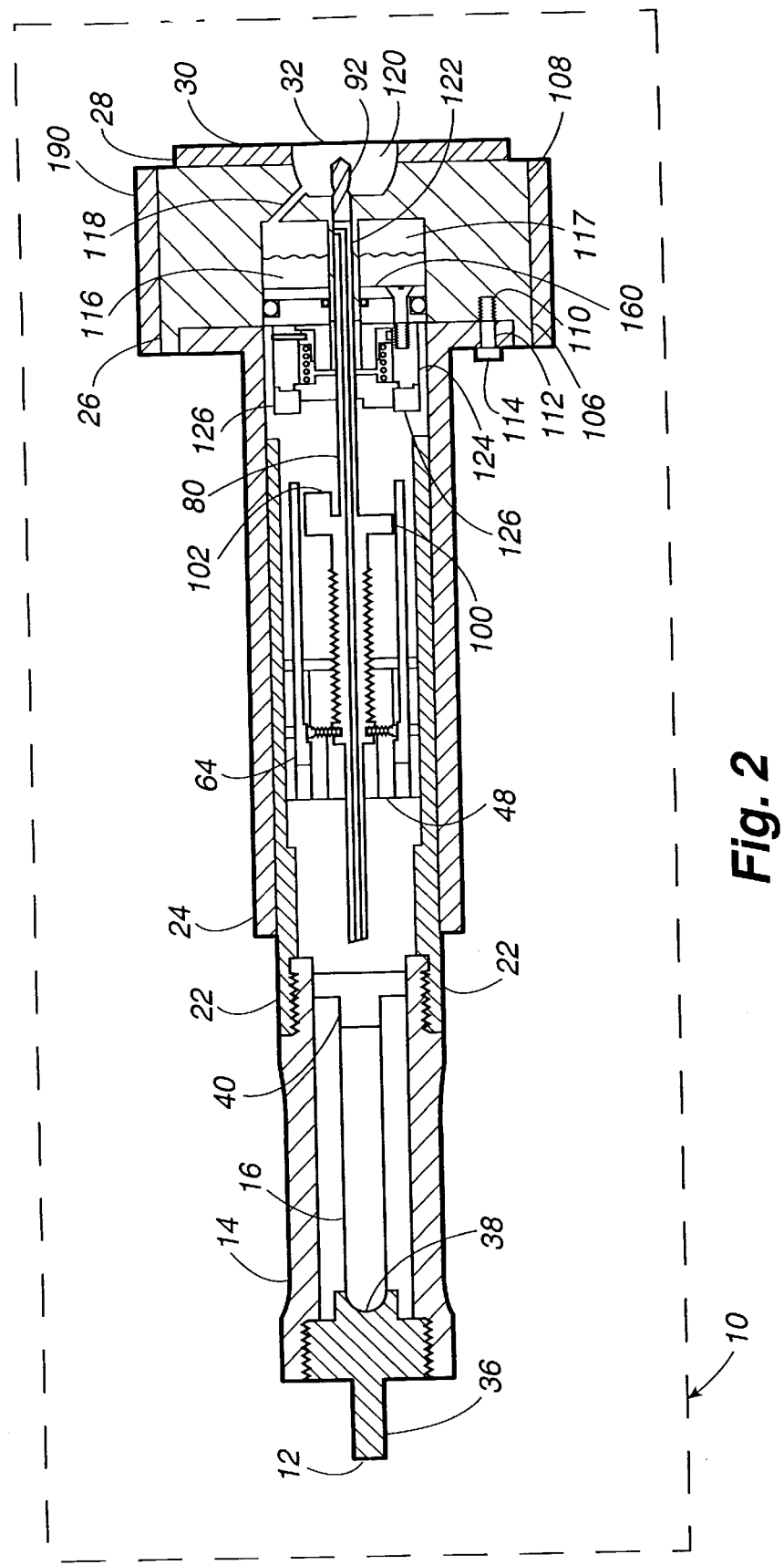
FIG. 2 shows a cross-sectional side view of the invention.

FIG. 2 shows a cross-sectional side view of tool 10, and FIGS. 3–9 show perspective and cross-sectional views of parts thereof. FIG. 2 shows tool 10 having a rod-like end member 36 threadably engaged to the sample container housing 14. End member 36 includes a shaft 12 and a receiving portion 38 adapted to receive the closed end of sample container 16. Generally, sample container 16 has a closed end and an open end that is sealed with a pierceable septum 40. Sample container 16 is evacuated prior to use, i.e. the pressure within sample container 16 is less than atmospheric pressure.

FIG. 2 includes a cross-sectional side view of barrel housing 22. FIGS. 3a–d show two cross-sectional side views of barrel housing 22, and adjacent to each side view is its corresponding top view. An axial rotation by 90 degrees of FIG. 3a and FIG. 3b produces FIG. 3c and FIG. 3d, respectively. FIG. 3d shows a pin groove 42 in barrel housing 22 for receiving pin 34. Threaded openings 44 in barrel housing 22 are adapted for receiving set screws 46 to engage and immobilize the barrel 48, which is shown in FIGS. 2 and 4.

Figure 4A:
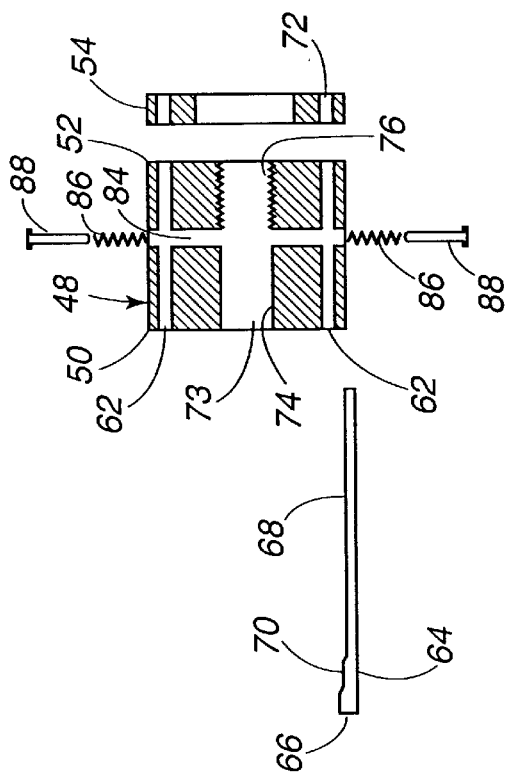
FIGS. 4a–b show exploded cross-sectional side views of the barrel of the invention.
Figure 4B:
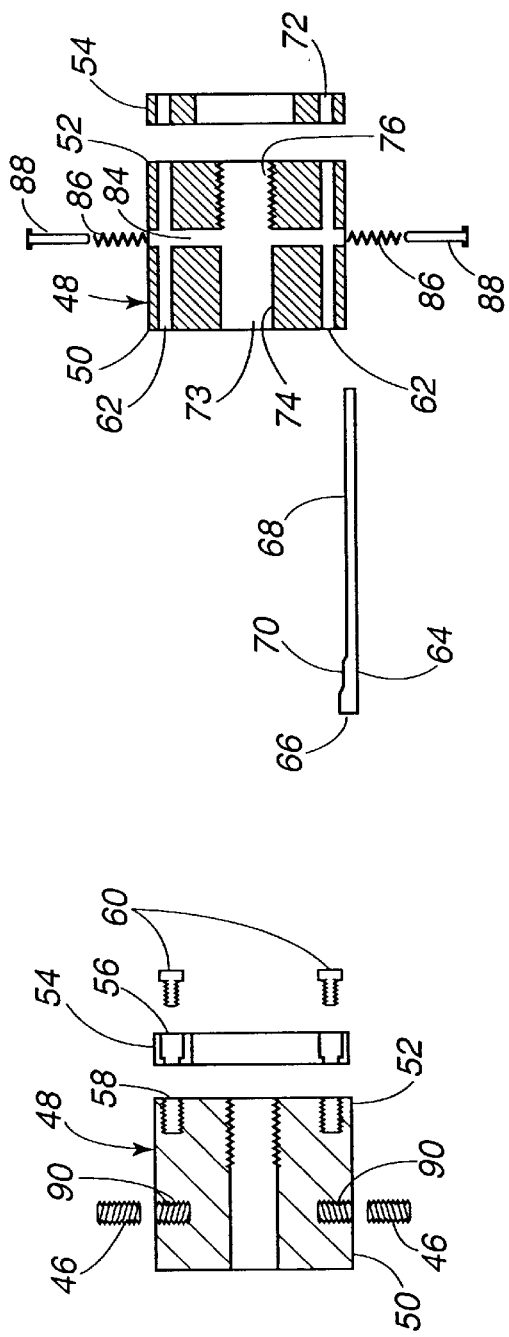

FIGS. 4a–b show two exploded cross-sectional side views of barrel 48; an axial rotation of FIG. 4a by 90 degrees produces FIG. 4b. Barrel 48 has a first end 50 and a second end 52. Disk 54 has openings 56 collinear with threaded openings 58 at second end 52 of barrel 48 so that disk 54 can be fastened to barrel 48 with screws 60. At least one rod passageway 62 is present in barrel 48, and is sufficiently wide for rod 64 to slide therethrough. The embodiment shown includes two rod passageways 62 for two rods 64. Each rod 64 has a wide portion 66, a narrow portion 68, and a flat middle portion 70 near wide portion 66 that is narrower than wide portion 66 but wider than narrow portion 68. When disk 54 is attached to barrel 48, disk passageways 72 overlap with rod passageways 62 in barrel 48. Disk passageways 72 are configured to allow narrow portion 68, but not flat portion 70, of rod 64 to pass therethrough. Barrel 48 also has an inner axial passageway 73 having a non-threaded inner surface portion 74 extending inward from first end 50, and a threaded inner surface portion 76 extending inward from second end 52. Threaded surface portion 76 receives threaded is section 78 of drilling member 80, shown in FIG. 2 and FIG. 5. When drilling member 80 is positioned within barrel 48 so that recesses 82a and 82b of drilling member 80 align with lateral passageway 84 in barrel 48, springs 86 and pins 88 are inserted into lateral passageway 84. Rod 64 is then pushed though rod passageway 62 until narrow end 68 of rod 64 passes though opening 72 in attached disk 54, and flat portion 70 of rod 64 compresses springs 86 against drilling member 80, and forces pins 88 into recesses 82a and 82b of drilling member 80; barrel 48 is then positioned in barrel housing 22 such that threaded lateral openings 90 in barrel overlap with threaded openings 44 in barrel housing. Barrel 48 is then attached to barrel housing 22 with screws 46. Now, barrel housing 22, barrel 48, and drilling member 80 will turn as a unit when rotated about their common axis.

Figure 5:
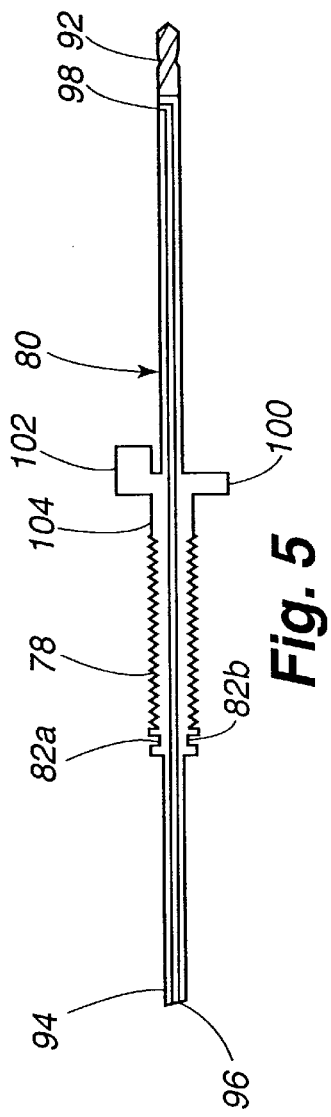
FIG. 5 shows a cross-sectional side view of the drilling member of the invention.

As shown in FIG. 5, drilling member 80 has a drilling end portion 92 and a piercing end portion 94. An axial passageway 96 extending from piercing end portion 94 throughout drilling member 80 intersects with an inlet 98 near drilling end portion 92. Drilling member 80 also includes cylindrical flange 100 having a raised portion 102 facing drilling end portion 92. A non-threaded portion 104 narrower than threaded portion 78 is located between threaded portion 78 and flange 100.

FIG. 2 also shows a cross-sectional side view of head member 26. Head member 26 has a first end 106 and a second end 108. Threaded openings 110 at first end are collinear with flange openings 112 in sleeve 24 so that head member 26 can be attached to sleeve with screws 114. Head member 26 has a cylindrical recess 116 into which is placed a chemical sealant 117. Preferable sealants include commercially available epoxy resins. Preferable sealants also include commercially available siloxanes and fluorosiloxanes that cure with when exposed to water vapor in humid air, at least partially, within seconds or minutes. Sealant passageways 118 between recess 116 and volume 120 of head member 26 are provided. An axial passageway 122 extending from first end 106 to second end 108 of head member 26 is provided for drilling end portion 92 of drilling member 80 to pass therethrough.

FIG. 2 also includes a cross-sectional side view of piston 124. FIGS. 6 and 7 show an enlarged and an exploded cross-sectional side view of piston 124, respectively, and FIG. 8 shows a perspective top and side view thereof. Piston 124 includes a ring-shaped end member 126 having an inner annular groove 128 shown in FIG. 7, and inner slots 130*a* and 130*b* shown in FIG. 8. Piston 124 also includes spring housing member 132 having a first end 134, a second end 136, an outer annular groove 138, and inner grooves 140*a* and 140*b* (shown in FIG. 7 but not in FIG. 8). End member 126 was brazed onto first end 134 of a spring housing member 132. As shown in FIG. 8, partial overlap of inner groove 140*a* with slot 130*a*, provides lip 142*a* above groove 140*a*. Similarly, but not shown in FIG. 8, partial overlap of inner groove 140*b* with slot 130*b* provides lip 142*b*, has shown in FIG. 6. Piston 124 also includes an o-ring housing member 144 having a cylindrical first end 146 and a cylindrical second end 148 having a larger diameter than first end 146. A circumferential groove 150 for an outer o-ring 152, and an inner annular groove 154 for an inner o-ring 156 are provided at second end 148. A disk-shaped capping member 158 prevents o-rings 152 and 156 from sliding out of grooves therein, and provides surface 160 that can contact sealant 117 within recess 116 of head member 26. Outer o-ring 152 and inner o-ring 156 provide a means to sealingly engage piston 124 to head member 26 and drilling member 80, respectively, to allow piston 124 to sealingly slide within head member 26, and to prevent sealant 117 in head member 26 from passing through piston during operation. Channels 162 in capping member 158 align both with channels 164 in o-ring housing member 144 and threaded holes 166 in spring housing member 132, so that screws 168 can attach capping member 158 to o-ring housing member 144 and to spring housing member 132.

FIG. 9 shows a perspective side-view of spring assembly 170. Spring assembly 170 includes a coil spring 172 and first spring flange 174 attached to one end of coil spring 172. First spring flange 174 has a raised portion 176 and an axial passageway 178 that is wide enough for drilling end portion 92 of drilling member 80 to pass therethrough. Spring assembly 170 also includes second spring flange 180 attached to the other end of coil spring 172. Second spring flange 180 has an axial passageway 181 wide enough for smaller cylindrical end 146 of o-ring housing member 144 to pass therethrough, as shown in FIG. 6. Flange 174 has circumferential protrusions 182*a* and 182*b* configured to slide into slots 130*a* and 130*b*, respectively, and then through grooves 140*a* and 140*b*, respectively. Spring assembly 170 is loaded into piston 124 by first sliding second spring flange 180 over the smaller cylindrical end 146 of o-ring housing member 144 and compressing coil spring 172 until protrusion 182*a* slides into slot 130*a* and protrusion 182*b* slides into slot 130*b*. First spring flange 174 is then rotated until protrusion 182*a* slides into groove 140*a* and contacts lip 142*a*, and protrusion 182*b* slides into groove 140*b* and contacts lip 142*b* as shown in FIG. 6; spring assembly 170 is now compressively engaged within piston 124. Second spring flange 180 has a circumferential groove 184 for receiving restraining screws 186 that are positioned within threaded openings 188 in piston 124, as shown in FIG. 6. Restraining screws 186 aid to minimize sliding of spring assembly 170 within piston 124 during use.

A brief description of how to use the invention now follows. Shaft 12 is clamped into the chuck of a rotatable drill. Tool 10 is pressed against a container wall so that sealing member 30 seals against the wall and opening 32 is covered by the wall. Pin 34 is removed, and the rotatable drill is activated. As tool 10 rotates, the position of phosphorescent stripe 20 is monitored. When stripe 20 is completely covered by sleeve 24, the drill is deactivated and tool 10 is moved away from the wall. Observation of a fluid sample within sample container indicates that successful sampling has taken place.

The following provides further details of the operation of the present invention. Upon activation of the rotatable drill, shaft 12, barrel housing 22, barrel 48 and rods 64 therein, and drilling member 80 rotate as a unit. While tool 10 is pressed against the container wall, drilling member 80 exits opening in head member 26, makes contact with the container wall, and bores a hole in the wall. Meanwhile, barrel housing 22 slides within sleeve 24, and barrel housing 22, barrel 48, rods 64, advance toward the wall. Drilling member 80 generates wall shavings during operation, which may be contaminated with fluid from the container. As they are generated, these wall shavings are confined and remain within volume 120 of head member. After drilling end portion 92 of drilling member 80 enters the container, inlet 98 near the drilling end portion 92 also enters the container. Fluid from within the container enters inlet 98 and passes through passageway 96 inside drilling member 80. Rods 64 continue to advance forward until they contact end member 126 of piston 124, after which they are forced to slide backward though rod passageways 62. As rods 64 slide backward, flat middle portions 70 of rods 64, which have been forcing pins 88 into recesses 82*a* and 82*b* in drilling member 80, lose contact with pins 88, whereupon springs 86 decompress and force pins 88 out of recesses 82*a* and 82*b* in drilling member 80, whereupon drilling member 80 is no longer forced to rotate with barrel 48. Drilling member 80, nevertheless, continues to advance with barrel 48 until flange 100, a part of drilling member 80, rotatably engages first spring flange 174 of spring assembly 170. Upon engagement, flange 100 causes a rotation of spring flange 174, which causes protrusions 182*a* and 182*b* on spring flange 174 to slide through grooves 140*a* and 140*b* respectively. When protrusions 182*a,b* are no longer in contact with lips 142*a,b*, protrusions 182*a* and 182*b* move through slots 130*a* and 130*b*, respectively, and spring assembly 170 decompresses and provides a compressive force against flange 100 of drilling member 80. As barrel housing 22 continues to advance toward container wall, the compressive force from spring assembly 170 prevents drilling member 80 from rotating and advancing with barrel housing 22, which causes drilling member 80 to move out of the borehole. Before drilling member 80 moves out of the borehole, piercing end portion 94 of drilling member 80 pierces septum 40 of the evacuated sample container 16, and fluid flows into sample container 16. As fluid collects inside sample container 16 and barrel housing 22 continues to advance toward the wall, barrel housing 22 contacts end member 126 of piston 124, and then forces piston 124 to slide within circumferential recess 116 of end member 26. As piston 124 moves, it forces sealant 117 out of recess 116, into passageways 118, and into volume 120. As drilling member 80 retracts from the borehole, sealant 117 is forced into the borehole. Meanwhile, the user is monitoring the circumferential stripe 20 on housing 14. Stripe 20 is positioned such that when it is completely obscured by sleeve 24, drilling member 80 is fully retracted from the borehole, and tool 10 has filled borehole with sealant 117. The rotatable drill can then be deactivated. The container wall is now plugged with sealant, and a fluid sample from the container has been obtained.

Many kinds of sealants for plugging the borehole can be used. Fluorosiloxane sealants, which are more expensive but more resistant to chemical attack than siloxane sealants, can be used with the present invention. When used with a siloxane or fluorosiloxane sealant, the present invention works best at obtaining fluid samples from containers having fluid that is not under extreme internal pressure (less than 5 kilopascals of pressure) since the pressurized fluid can force the sealant out of the borehole before it hardens. Various low melting solid materials having melting points between about 25–100° C., such as low-melting metal alloys and thermoplastics, can also be used as sealants; they are placed into recess 116 of head member 26 during assembly of tool 10, and head member 26 is heated to melt the glue or thermoplastic prior to use. Head member 26 can be heated by known heating means, such as a hot plate, heating tape 190 wrapped around head member 26, etc. After the solid materials melt, tool 10 can be used as precisely described. The warmed sealants cool and resolidify after entering the borehole and seal the borehole. Clearly, one would not use a warmed sealant to sample a fluid if it is known that a component of the fluid has a flash point below the melting temperature of the sealant. If the present invention is used to obtain samples from cryogenic containers, the chemical sealant does not need to be heated above room temperature.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A tool for collecting a fluid sample through a container wall, comprising:
   a. an elongated drilling member having a drilling end, a fluid-withdrawing end, an inlet near said drilling end, an outlet at said fluid-withdrawing end, an internal passageway providing fluid communication between the inlet and the outlet, and an externally threaded portion between said drilling end and said fluid withdrawing end;
   b. means for rotating said drilling member, whereby said drilling end drills a borehole into the container wall thereby generating wall shavings, whereby fluid enters the drilling member through the inlet and flows into the internal passageway therein;
   c. means for withdrawing fluid through the fluid-withdrawing end of said drilling member;
   d. means for retracting the drilling member from the borehole;
   e. a chemical sealant for sealing the borehole; and
   f. means for forcing said chemical sealant into the borehole.

2. The tool of claim 1, further including a head member having a sealing surface to seal said head member to the wall, a recess for storing said chemical sealant, a volume for receiving wall shavings generated from drilling the borehole, and a passageway so that sealant can move out of the head member and into the borehole.

3. The tool of claim 2, wherein said fluid withdrawing means is a sealed container comprising a tubular body having an open end and a closed end, and a septum sealing the open end and capable of being pierced by said fluid withdrawing end of said drilling member, the sealed container having an internal pressure less than atmospheric pressure.

4. The tool of claim 3, further comprising a cylindrical barrel member having a first end, a second end, and an inner axial passageway therethrough, the passageway having a threaded inner axial surface portion along said inner axial passageway for receiving said threaded portion of said drilling member.

5. The tool of claim 4, further comprising a rotatable tubular housing surrounding said sample container and said drilling member and said barrel member, said housing being attached to said cylindrical barrel member so that said housing and said barrel member must rotate as a unit.

6. The tool of claim 5, wherein said chemical sealant has a melting temperature of less than about 100° C.

7. The tool of claim 6, wherein said chemical sealant is chosen from the group consisting of siloxanes, fluorosiloxanes, and epoxy resins.

8. The tool of claim 6, wherein said tool further includes means for heating said chemical sealant.

9. The tool of claim 8, wherein said chemical sealant is chosen from the group consisting of metal alloys and thermoplastics.

10. The tool of claim 8, further including a tubular sleeve member wide enough to slide around said tubular housing member, said sleeve member having a flange at one end configured for attachment to said head member.

11. The tool of claim 10, wherein said tubular housing includes an external marking used to indicate when fluid sampling is completed.

* * * * *